United States Patent [19]

Ales et al.

[11] Patent Number: 4,642,819
[45] Date of Patent: Feb. 17, 1987

[54] DISPOSABLE GARMENTS WITH MULTIPLE STRAND ELASTICIZED OPENINGS

[75] Inventors: Thomas M. Ales, Winnebago County; David T. Strohbeen, Outagamie County; Joyce A. Damico, Winnebago County, all of Wis.

[73] Assignee: Kimberly-Clark Corporation, Neenah, Wis.

[21] Appl. No.: 690,349

[22] Filed: Jan. 10, 1985

[51] Int. Cl.⁴ .............................................. A61F 13/16
[52] U.S. Cl. ........................................... 2/400; 2/402; 2/270; 604/385 A
[58] Field of Search .................. 2/400, 401, 402, 403, 2/221, 270; 604/385.2, 392, 378, 391, 358, 396

[56] References Cited

U.S. PATENT DOCUMENTS 4,031,568  6/1977  Huff ...................................... 2/402 X
4,300,562 11/1981  Pieniak ............................... 604/385.2
4,333,782  6/1982  Pieniak ............................... 604/385.2
4,556,596 12/1985  Meuli ................................... 2/270 X

FOREIGN PATENT DOCUMENTS

69/8338  7/1970  South Africa .

Primary Examiner—Werner H. Schroeder
Assistant Examiner—J. L. Olds
Attorney, Agent, or Firm—Douglas L. Miller; Donald L. Traut; Jeremiah J. Duggan

[57] ABSTRACT

A disposable garment (10) having at least one opening (13) elasticized with two or three spaced elastic elements (30) having a cross-sectional shape with an aspect ratio of 0.25 to 1, its shortest axis about 0.8 to 3.2 mm long and a cross-sectional area of about 0.5 to 8 mm². In particular, a disposable garment (10) having leg openings (13) elasticized with two or three such spaced elastic elements (30) and a waist opening (12) elasticized with a flat elastic ribbon (70).

7 Claims, 7 Drawing Figures

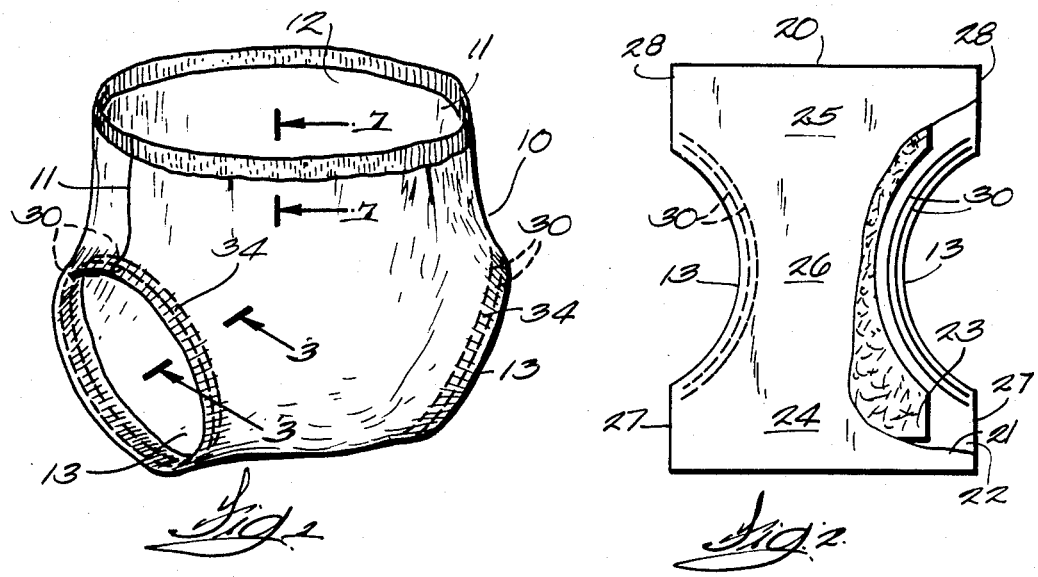
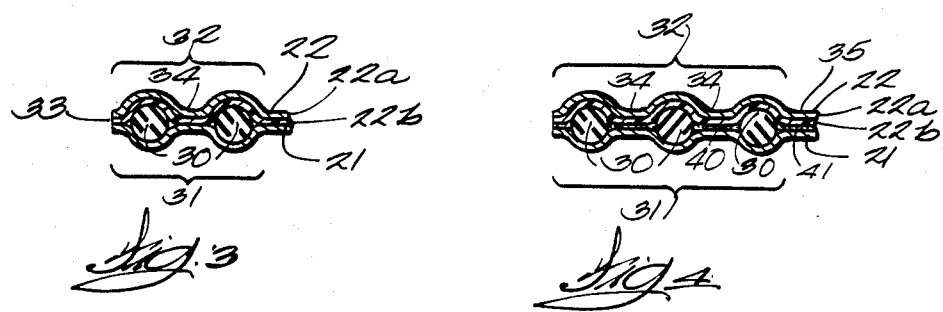
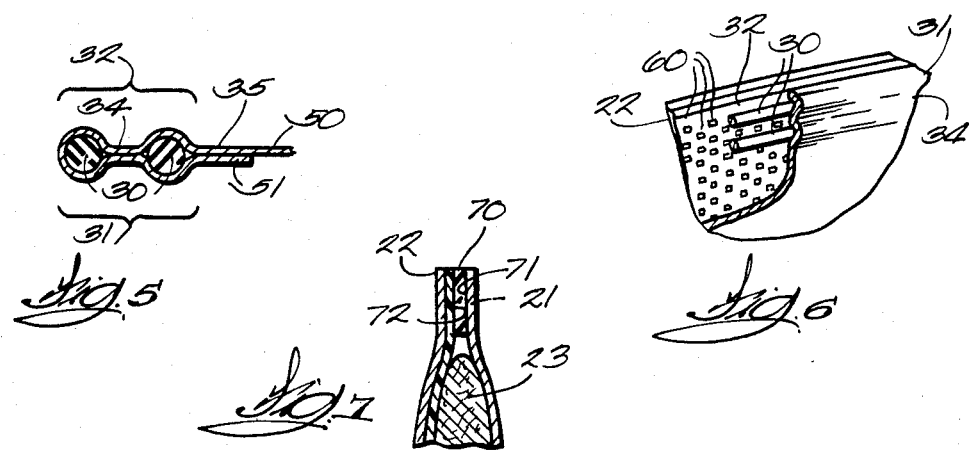

DISPOSABLE GARMENTS WITH MULTIPLE STRAND ELASTICIZED OPENINGS

TECHNICAL FIELD

This invention relates generally to the field of disposable garments; more specifically, this invention relates to elastic constructions which may be used around openings of disposable garments, such as along a person's waist, leg, ankle, neck or wrist.

BACKGROUND ART

The term "disposable garments" is defined herein to means articles intended to be worn by persons, including infants and adults, which are designed for single use or temporary use and are meant to be disposed of after being used instead of being laundered or dry cleaned for re-use. Examples of disposable garments include diapers; adult incontinence garments; hospital garments such as surgical gowns, caps and booties or shoe covers; single use garments intended to be worn by patients in a hospital such as disposable pajamas and gowns; and various other types of garments, such as laboratory coats, shower caps, etc. Single use or disposable garments are most usually made of lightweight film or sheet material such as thermoplastic films, nonwoven sheets of thermoplastic or cellulosic fibers, papers, coated films or papers and various composites of one or more of these types of materials. The materials for disposable garments are distinguishable from textiles that are used to make a sewn garment or article intended for long term use and subject to repeated laundering or drycleaning. Further, disposable garments must generally be manufactured using techniques such as die-cutting, heat sealing, sonic sealing, adhesive bonding, etc., that facilitate high speed low cost production of disposable garments, instead of the sewing methods customarily employed to produce textile garments.

Disposable garments may employ some form of elasticized body-encircling opening in order to provide a form-fitting closure around part of a person's body. A disposable diaper will often have elasticized leg openings in order to reduce leakage around an infant's legs, or sometimes an elasticized waist opening; a gown or coat-like disposable garment may have elasticized wrist openings to provide a snug fit about a person's wrists; disposable booties or shoe covers may have an elasticized ankle-encircling portion; and a disposable cap may have an elasticized opening to fit about a person's head.

Thus, for example, a typical disposable diaper structure will include an elastic element along each of the leg openings of the diaper. The elastic elements most generally described in patents relating to this type product have been thin, flat tapelike elements with a small aspect ratio. The term "aspect ratio" as used in this description and the claims is defined as the ratio of two perpendicular axes of the cross-sectional shape of an elastic element, one being the shortest axis of the cross-sectional shape and the other being the axis perpendicular thereto. Thus, for example, U.S. Pat. No. 4,860,003 (Buell) discloses a thin elastic strip 0.007 inches thick by 0.25 inches wide, having as aspect ratio of only 0.028. U.S. Pat. No. 4,325,372 (Teed) discloses only flat ribbon-like elastic elements without stating any specific dimensions. U.S. Pat. No. 4,430,086 (Repke) describes elastic elements along each leg opening of the diaper which are to have a thickness of 0.010 inches or less, preferably 0.0005 to 0.005 inches thick; no width is given in the patent, but it appears that the patent relates only to a thin, flat type of elastic element which would have a very low aspect ratio. U.S. Pat. No. 4,300,562 (Pieniak) describes an elastic element said to be suitable for disposable diapers consisting of a ladder-like structure having a plurality of longitudinal elements of circular cross-section connected by transverse elements in which the longitudinal elements have varying diameters. U.K. application No. 2 056 910 (Pieniak et al), published Mar. 25, 1981, discloses a similar structure in which each longitudinal element has the same diameter. These latter two specifications describe the ladder-like elements as being from 0.001 to 0.050 inches thick and from 0.25 to 2 inches wide, thereby resulting in elastic elements with an aspect ratio in the range of 0.005 to 0.20. There are also patents or published applications that describe the use of multiple elastic strands along an elasticized opening. U.S. Pat. No. 4,050,462 (Woon et al) discloses multiple strands as being suitable for elastic means along the legs of a disposable diaper. The aforesaid recently-issued U.S. Pat. No. 4,430,086 also discloses two separate elastic elements along a leg opening of a disposable diaper. U.K. application No. 2 118 021 (Migaku et al), published Oct. 26, 1983, describes a construction incorporating from 3 to 45 elastic strings along an elasticized leg opening in a diaper; while the strings have an aspect ratio of 1.0 since they have a circular cross-section, they are very small in diameter with a cross-sectional area of only 0.03 to 0.045 mm$^2$. The foregoing disclosures notwithstanding, we are not aware of any prior art teaching regarding elastic elements having a relatively high aspect ratio nor of any commercially-available disposable garment utilizing such elastic elements.

DISCLOSURE OF THE INVENTION

Our present invention provides elastic means for a disposable garment consisting of two or three elastic elements each having a cross-sectional area in the range of about 0.5 mm$^2$ to 8 mm$^2$ and an aspect ratio in the range of about 0.25 to 1 with the shortest axis of its cross-sectional shape from about 0.8 mm to 3.2 mm long. The elastic elements are separate and independent of each other and are joined in spaced relationship to two layers of material of which a disposable garment is made along an opening intended to fit snugly about a person's body.

DESCRIPTION OF THE DRAWINGS

The present invention is described below by reference to the following drawings in which:

FIG. 1 is a perspective view of a disposable panty incorporating elasticized leg openings according to the present invention;

FIG. 2 is a plan view of a blank from which the garment of FIG. 1 can be made;

FIG. 3 is a sectional view of an elasticized leg opening of the garment of FIG. 1;

FIG. 4 is a sectional view of an alternate contruction of an elasticized opening, such as the leg openings of the garment of FIG. 1;

FIG. 5 is a sectional view of another alternate construction for an elasticized opening according to the present invention;

FIG. 6 is a plan view of a section of the garment of FIG. 1 illustrating a preferred mode for joining the elastic elements to the garment; and FIG. 7 is a sectional view of the elasticized waist opening of the garment of FIG. 1.

BEST MODES FOR CARRYING OUT THE INVENTION

FIG. 1 is a perspective view of a disposable panty 10 formed from a blank of material which has been cut to the appropriate configuration, folded and joined along side seams 11 to provide a panty having a waist opening 12 and a pair of leg openings 13 separated by a central crotch portion.

FIG. 2 illustrates a blank 20 suitable for the formation of the panty 10. The blank 20 includes a bodyside liner 21 and an outer cover 22, with an absorbent batt 23 sandwiched between the liner and the cover. The absorbent batt may be attached to the outer cover or the liner, or both, by any of the techniques generally known in the art, such as by glue lines or spots, sonic sealing, heat sealing, adhesive tapes, etc., in order to form the composite structure. Marginal portions of the outer cover 22 and liner 21 surrounding the batt may be joined to one another by such techniques or may be joined by the elastic elements described below. The blank 20 has an hourglass shape with leg openings 13 cut in the desired curvature, thus defining a front portion 24 and rear portion 25 connected together by a central crotch portion 26. The blank is folded transversely along the crotch portion so that a side 27 of the front portion at one end of a leg opening contacts a side 28 of the rear portion on the opposite end of a leg opening and the contacting sides 27 and 28 are secured to one another along the side seams 11 to form the panty 10.

As illustrated in FIG. 2, a pair of spaced elastic elements 30 are positioned about each leg opening 13. Each elastic element 30 is shown as curvelinear to generally match the curvature of each leg opening. The structure of the elements 30 and their joinder to a disposable garment, in accordance with this invention is illustrated in detail in the cross-sectional view of FIG. 3. The bodyside liner 21 and the outer cover 22 of the panty each have a marginal portion surounding a leg opening 13. (It will be noted in FIG. 3 that the outer cover 22 is shown as including an outer layer 22a and inner layer 22b.) The marginal portion of the liner 21 along each leg opening extends about the interior of a leg opening to provide interior marginal portion 31 and the marginal portion of the outer cover 22 extends about the exterior of each leg opening to provide exterior marginal portion 32. Thus, the exterior marginal portion 32 extends about the outside of a leg opening with reference to the manner in which the panty 10 is normally worn, and the interior marginal portion 31 extends about the inside of a leg opening. The elastic elements 30 are positioned between the interior marginal portion 31 and exterior marginal portion 32, and the exterior surface of each element 30 is joined to both the interior and exterior marginal portions. The free ends of both the interior and exterior marginal portions, which form the boundary of a leg opening, are located adjacent the outermost element 30, as indicated at 33. The elastic elements 30 are spaced from one another along the leg opening 13 so that there is a zone 34 of the interior and exterior marginal portions between the elements 30 along which the marginal portions are not joined to each other in the embodiment of FIGS. 1–3. Two spaced elastic elements 30 are illustrated in FIGS. 1–3, but the instant invention may also be practiced with three spaced elastic elements 30 as illustrated in the sectional view of FIG. 4, which corresponds to the section of FIG. 3, there also being a zone 34 between each element 30 in this alternate construction.

An alternate structure for the interior and exterior marginal portions in combination with elastic elements 30 in a disposable garment is also illustrated in the sectional view of FIG. 4. The sections of the interior and exterior marginal portions 31 and 32 within a zone 34 between the spaced elastic elements 30 are joined together along a layer of adhesive 40. The interior and exterior marginal portions may be joined together within the zones 34 by other suitable means, such as by sonic sealing, heat sealing and the like. Sections of the interior and exterior marginal portions may also be joined together by means of adhesive layer 41 along a zone 35 positioned adjacent to the innermost elastic element 30. Zones 34 and 35 extend circumferentially about an elasticized opening, as shown with respect to a zone 34 about a leg opening 13 in FIG. 1. The sections of the interior and exterior marginal portions 31 and 32 should be intermittently joined together circumferentially about the circumference of an opening in a zone 34 or 35.

FIG. 5 illustrates the manner in which elastic elements may be attached to a single layer garment, which drawing corresponds to the sectional drawings of FIGS. 3 and 4. The layer 50 of a disposable garment extends about spaced elastic elements 30 so as to have an exterior marginal portion 32 along the opening to be elasticized which is on the outside of the garment, and is then folded over the outermost elastic element to have a folded-over portion 51 which extends along the opposite surface of the elements 30 to provide an interior marginal portion 31 of the garment material. The sections of the interior and exterior marginal portions 31 and 32 within the zone 34 between the elements 30 can be joined together in the manner described in connection with FIG. 4, and the marginal portions also can be joined together along zone 35 adjacent the innermost element 30 as shown in FIG. 4.

In the foregoing constructions, the elastic elements 30 are joined to the garments during fabrication thereof when in a stretched or elongated condition. When fabrication is completed, the elastic elements are allowed to retract and thereby provide an elasticized opening that can be expanded to provide a snug fit about a person's body along the elasticized opening.

The waist opening 12 can be elasticized with the same constructions as described above in connection with the leg openings 13. However, the waist opening can be elasticized with a different structure, such as a flat tape-like elastic member as described below in greater detail.

The elastic elements 30 in accordance with the present invention are to have a cross-sectional shape with a substantial aspect ratio and area. Specifically, the aspect ratio of the cross-sectional shape of the elastic elements is to be in the range of 0.25 to 1, the shortest axis of the cross-section is to be in the range of about 0.8 to 3.2 mm long, and the cross-sectional area is to be in the range of about 0.5 to 8 mm$^2$, preferably about 1.5 to 2.5 mm$^2$. Various cross-sectional geometric configurations can be employed for the elastic elements, such as the circular cross-sectional shape illustrated in FIGS. 1–6 which has an aspect ratio of 1, cross-sections with a minor axis and a major axis such as elliptical and oval shapes that will have an aspect ratio less than 1 but within the above stated range, a square cross-sectional shape which also will have an aspect ratio of 1, a rectangular cross-sectional shape which will have an aspect ratio less than 1 but within the above stated range, a hexagonal cross-sectional shape, as well as other geometric configurations having the stated parameters. The elastic elements along an opening can each have the same cross-sectional shape or they can have different cross-sectional shapes.

Elastic elements of the stated parameters have several characteristics that are important during manufacture of a disposable garment and which have an impact on the functionality of a finished garment. It has been found that the above parameters provide elastic elements having sufficient elasticity to provide a good fit about a body-encircling opening, such as the leg openings 13 in the panty described above, and also provide an elasticized opening which will reduce or prevent the leakage of waste fluids about an elasticized opening. Elastic elements with cross-section dimensions less than the stated range are not considered suitable for such purposes and have the further disadvantage of being extremely difficult to handle during the manufacture of a disposable garment. Additionally, it has been found that elastic elements with the specified cross-sectional dimensions can be more readily secured to a disposable garment in an arcuate condition such as illustrated in FIG. 2 so that they can be arranged to parallel the curvature of a cut-out portion of a disposable garment. Flat, wide elastic elements are more difficult to arrange in this fashion, and are therefore generally placed in a garment as straight or rectilinear elements in prior art constructions instead of an arcuate condition. Spacing between elastic elements in the range of about 3 to 13 mm (⅛ to ½ inch) is suitable for most disposable garments, although spacing outside this range also can be used.

The use of two or three spaced independent elastic elements 30 of cross-sectional dimensions as described above has further advantages in that it allows the use of elastic elements of differing dimensions in order to control the stretch characteristics of an elasticized opening, or the use of different types of elastomeric material for the spaced elastic elements to also aid in the controlling the stretch of an opening. Also, because the elastic elements are separate and independent, each can be attached to a disposable garment at a different degree of elongation, thereby providing additional control of the characteristics of an elasticized opening. It has further been found that en elasticized opening, such as a leg opening, can be produced with the instant invention using a lesser total amount of elastic material than is the case with flat, wide elastic elements but still achieving the same functionality as to fit and fluid sealing; this is an important achievement since elastic material can represent a significant cost in a disposable garment. The interior and exterior marginal portions of a garment in the zones between spaced elastic elements can take on a pleated or ribbed effect when the elastic elements are retracted to thereby provide an attractive and pleasing appearance to the finished garment, such as has not been obtained with prior art constructions.

Any suitable elastomeric material can be employed for the elastic elements 30 in the practice of this invention that exhibits a percentage elongation (defined herein as $L_s - L_r / L_r \times 100$ where $L_s$ is the stretched length of the elastic element, and $L_r$ its retracted length) at least in the range of 5% to 300%, preferably in the range of 75% to 200% and most preferably in the range of 100% to 150%. Various commercially available materials can be used, such as natural rubber, butyl rubber or other synthetic rubbers, thermoplastic materials that become elastic upon being heated, urethane elastomeric material such as that available from B. F. Goodrich Company under the tradename TUFTANE, and self-adhesive elastomeric material such as that available from H. B. Fuller Company under the tradename FULLASTIC. The latter material (see e.g. U.S. Pat. No. 4,418,123) is based upon thermoplastic elastomeric co-polymers of the A-B-A type such as those available from Shell Chemical under the trademark KRATON which have a rubbery midblock of butadiene or isoprene and polystyrene end blocks, and is especially useful because it is a self-adhesive material and can be joined to the layers of a disposable garment without additional adhesive between the elastic element and the layers. The elastic elements also can be applied to the garment by adhesive bonding, heat sealing or sonic bonding when appropriate to the specific material selected for the elastic elements.

The joinder of the elastic elements 30 to the interior and exterior marginal portions of a garment as described above can be of various configurations. For example, the interfacial joinder may extend along the length of each elastic element or may extend only along discrete separate zones of the interfacial contact. Thus, joinder may take place along part of the interface between the elastic elements and marginal portions or along most of the interface between these members. The particular configuration selected for the joinder of the elastic elements to the marginal portions will depend upon both the functionality and the appearance desired for a specific garment. An especially useful technique for joining the elastic elements 30 to marginal portions of a garment is described and claimed in the application of Thomas M. Ales et. al. entitled Elastic Form-Fitting Enclosure Constructions for Disposable Garments, U.S. Ser. No. 690,348 filed on the same date herewith and assigned to the assignee of this application. FIG. 6 illustrates spaced elastic elements 30 joined to an exterior marginal portion 32 of outer cover 22 and an interior marginal portion 31 of bodyside liner 21 in accordance with said application. The innermost surface of the outer cover 22 in contact with the elastic elements 30 includes a plurality of spaced bond points 60. The surface of each element 30 in contact with the exterior marginal portion is joined to the bond points with the elastic elements in a stretched condition during fabrication of the garment, and may also be joined to material between the bond points. The elastic elements are retracted during a final stage in the fabrication process and remain joined only to the bond points in the finished garment but are separated from material between the bond points to which they may have been joined during fabrication. This results in micro-ribbing or micro-buckling of the exterior marginal portion of the outer cover between the bond points to thereby form an elasticized opening having a very finely-ribbed exterior structure along the opening. This construction is described in greater detail in the aforesaid application, the disclosure of which is incorporated herein by reference.

The layer or layers of material from which a disposable garment is made incorporating the elastic construction of the present invention can be any of the materials appropriate for the manufacture of disposable garments. Suitable materials comprise nonwoven fibrous webs of synthetic and/or natural fibers, including: a spun-bonded nonwoven web of synthetic fibers such as polypropylene, polyethylene or polyester fibers; a nonwoven web of cellulosic fibers, textile fibers such as rayon or cotton fibers and the like, or a blend of cellulosic and textile fibers; a spun-bonded nonwoven web of synthetic fibers mixed with cellulosic, pulp or textile fibers; or melt blow thermoplastic fibers, such as macrofibers or microfibers, of polypropylene, polyester, polyethylene or other thermoplastic materials, or mixtures of such thermoplastic fibers with cellulosic pulp or textile fibers. Also suitable are plastic materials in the form of films including: polyolefin polymers, such as polyethylene or polypropylene; polyolefin copolymers such as ethylene vinyl acetate, ethylene methyl acrylate or ethylene ethyl acrylate; polyvinyl chloride; or nylon. In addition, composite webs incorporating an outer layer of the foregoing types of nonwoven fibrous materials and an inner layer of the foregoing types of plastic materials can be utilized; thus with respect to FIGS. 3 and 4, the outer layer 22a of the outer cover 22 can be a nonwoven fibrous material and the inner layer 22b a plastic material as described and claimed in the application of William M. Heran et al entitled Disposable Underpants, Such As Infant's Training Pants and the like filed on the same date herewith, U.S. Ser. No. 690,351, and assigned to the assignee of this application, which is incorporated herein by reference. The materials for a particular garment must be selected with a view towards the end use of the garment. For example, a disposable diaper or disposable panty may employ a bodyside liner of liquid-pervious nonwoven fibrous material to provide a soft inner liner that will be comfortable against the wearer's skin, and an outer cover of a liquid-impervious plastic material or a composite fiber and plastic material in order to impart moisture and fluid barrier functionality for the garment. Other disposable garments such as disposable gown, booty, etc., can be made from a single layer of nonwoven fibrous material, for example, and may not require plastic material if moisture barrier is not a necessary characteristic.

An absorbent batt when included in a disposable garment, such as the absorbent batt 23 of the disposable panty 10, may comprise any suitable material capable of absorbing and retaining waste fluids that pass through the bodyside liner. The absorbent batt may comprise cellulosic material such as an air-formed batt of wood pulp fibers, commonly known as "fluff"; a batt of melt blown synthetic fibers, such as of polypropylene, polyethylene, polyester and the like; a bonded carded web of synthetic or cellulosic fibrous materials; a combination of melt blown fibers of polypropylene, polyethylene polyester or the like mixed with pulp fibers; or a blend of fluff with staple textile fibers such as rayon and the like. The batt may comprise one or more layers or combinations of the foregoing materials. In addition, the batt may include compounds added to increase its absorbency.

A particularly useful combination for a disposable panty has been found to include a flat elastic ribbon or tape-like member along the waist opening of the panty and spaced elastic elements such as the elements 30 along the leg openings of the garment. Thus, with reference to the panty 10 of FIG. 1, the leg openings 13 may be elasticized by two or three spaced elastic elements as previously described in detail with connection with FIGS. 2–6. The waist opening 12 is elasticized, referring now to FIG. 7, by a flat elastic ribbon 70 having a flat inner surface 71 joined to the bodyside liner 21 and a flat outer surface 72 joined to the outer cover 22 about the waist opening 12. The elastic ribbon 70 may be of the same materials as previously described in connection with the elastic elements 30. Most usefully, the elastic ribbon 70 should have flat opposed surfaces 71 and 72 that are from about 9.5 to 19 mm ($\frac{3}{8}$ to $\frac{3}{4}$ inch) wide and the ribbon 70 should be in the range of about 0.25 to 0.5 mm (0.010 to 0.020 inch) thick. An elastic ribbon 70 provides a waist opening with sufficient tension to hold a panty on the person wearing it and also provides an elasticized waistband which is stiff enough to prevent folding over and yet flexible enough to be comfortable. The spaced elastic elements 30 at the leg openings of the panty provide effective sealing or gasketing against the leakage of waste fluids through the leg openings. Thus, the waist elastic provides means for suspending the panty about the wearer and the elastic elements at the leg openings provide closure means around the wearer's legs. In a disposable underpant such as the panty 10, the absorbent batt 23 is a relatively stiff or bulky material as compared to the other layers of the garment and tends to push an elastic member at the leg openings away from a person's body, thereby causing the leakage of waste fluids through the leg openings. By using two or three spaced elastic elements 30 along the leg openings, each elastic element acts independently of the others. Therefore, in the case of employing three elastic elements 30 at the leg openings, for example, the absorbent will tend to lift the innermost elastic element 30 away from the body as the person moves about, may lift the intermediate or middle elastic element to a lesser extent, but will not tend to lift the outermost element 30. It appears that some of the displacement about the leg openings is taken up by the zones 34 between the spaced elastic elements 30. The outermost element 30 provides sealing against the leakage of fluids through the leg openings, and the intermediate element 30 also provides a measure of sealing against leakage. Thus, the use of spaced elastic elements 30 at the leg openings results in flexible elasticized openings that are better capable of resisting physical displacement by the action of the batt and therefore more capable of retaining effective gasketing against the leakage of fluids through the leg openings, all in comparison to a flat elastic ribbon such as the member 70.

EXAMPLE

A disposable panty such as the panty 10 illustrated in FIG. 1 was constructed in a size suitable for use as an infant's training panty with an elasticized waist opening as shown in FIG. 7 and elasticized leg openings as shown in FIG. 4. The material of the outer cover, or exterior panel, of the disposable panty was a two-layer composite web having an outer layer of nonwoven polypropylene fibers and an inner layer of ethylene methyl acrylate extrusion coated onto the nonwoven fibrous outer layer. The panty had an interior panel comprising a bodyside liner of spun bonded polypropylene fibers. An absorbent batt of a composite of polypropylene microfibers and cellulosic fibers was sandwiched between the exterior panel and the interior panel. The elastic member along the waistband was a flat ribbon about 19 mm ($\frac{3}{4}$ inch) wide and about 0.3 mm (0.012 inch) thick consisting of an A-B-A self-adhesive elastomeric copolymer (FULLASTIC) as described above.

Three strands of the same elastomeric copolymer were arranged about each leg opening; the strands had a circular cross-section with a diameter of about 1.58 mm (1/16 inch), an aspect ratio of 1 and a cross-sectional area of about 1.96 mm². The strands were spaced about 6.35 mm (¼ inch) apart. The elastic member at the waist opening was stretched about 160% and the elastic elements at the leg openings were stretched about 114% of their original lengths and joined to the exterior panel and the interior panel around the waist and leg openings respectively, and then allowed to retract to their original lengths to form the finished garment. Tests of the garment with infants demonstrated that the underpant remained securely held in place about an infant's waist when the waist elastic was expanded as the garment was fit onto an infant and that the elasticized leg openings provided good sealing or gasketing against the leakage of fluids therethrough.

We claim:

1. In a disposable garment of the type having at least one opening intended to fit snugly about a wearer's body, which opening is defined by an exterior marginal portion of material and an interior marginal portion of material together with elastic means joined thereto to provide an elasticized opening for the garment, the improvement wherein:
   (1) the elastic means consists of a plurality of elastic elements positioned between the exterior marginal portion and the interior marginal portion, and extending substantially about the periphery of the opening;
   (2) each elastic element has a cross-sectional shape having an aspect ratio in the range of 0.25 to 1 with its shortest axis in the range of about 0.8 to 3.2 mm long and an area in the range of about 0.5 to 8 mm²; wherein each elastic element can have a cross-sectional shape, an aspect ratio, and an area different from the other elastic elements to provide different elastic characteristics thereto;
   (3) each elastic element is joined to both the exterior marginal portion and the interior marginal portion in a stretched condition to provide an elasticized opening when in a retracted condition; and
   (4) the elastic elements are spaced from one another in a direction transverse to the direction of stretch of the elements, there beng an unbroken continuous zone of the exterior marginal portion and interior marginal portion between adjacent spaced elastic elements and extending substantially about the periphery of the opening.

2. A disposable garment according to claim 1, wherein:
   the exterior marginal portion is part of an outer layer of the disposable garment, and the interior marginal portion is part of an inner layer of a disposable garment.

3. A disposable garment according to claim 1, wherein:
   the exterior marginal portion is part of one layer of a disposable garment, and the interior marginal portion is a part of the same layer of the garment folded-over to contact each spaced elastic element.

4. A disposable garment according to claim 1, 2, or 3 wherein:
   the exterior and interior marginal portions of material are joined to one another within each zone between spaced elastic elements.

5. A disposable panty comprising, in combination:
   an outer cover, a bodyside liner and an absorbent batt therebetween arranged to provide a panty including a front portion and a rear portion interconnected by a central crotch portion, and side seams joining together contacting marginal sections of the front portion and rear portion to define a waist opening and a pair of leg openings;
   an exterior marginal portion of the outer cover along each leg opening, and an interior marginal portion of the bodyside liner along each leg opening, each leg opening further including:
   (a) two or three spaced elastic elements extending substantially about the periphery of the leg opening, each having a cross-sectional shape having an aspect ratio in the range of 0.25 to 1 with its shortest axis in the range of about 0.25 to 3.2 mm long an an area in the range of about 0.5 to 8 mm² wherein each elastic element can have a cross-sectional shape, an aspect ratio, and an area different from the other elastic elements,
   (b) each elastic element being joined to both the exterior marginal portion of the outer cover and the interior marginal portion of the bodyside liner along its respective leg opening, and
   (c) an unbroken continuous zone of the exterior marginal portion of the outer cover and the interior marginal portion of the bodyside liner between adjacent spaced elastic elements along each leg opening, and extending substantially about the periphery of each leg opening, each elastic element being joined at its respective leg opening in a stretched condition to provide an elasticized leg opening when retracted.

6. A disposable panty according to claim 5, further including:
   an exterior marginal portion of the outer cover and an interior marginal portion of the bodyside liner along the waist opening, and an elastic ribbon joined therebetween,
   the elastic ribbon having a pair of opposed flat surfaces, one joined to the exterior marginal portion of the outer cover and the other joined to the interior marginal portion of the bodyside liner.

7. A disposable panty according to claim 6 wherein the flat surfaces of the elastic ribbon are in the range of about 9.5 to 19 mm wide and the elastic ribbon is in the range of about 0.25 to 0.5 mm thick.

* * * * *